United States Patent [19]
Hagiwara et al.

[11] Patent Number: 5,244,667
[45] Date of Patent: Sep. 14, 1993

[54] SILICA-GEL BASED ANTIMICROBIAL COMPOSITION HAVING AN ANTIMICROBIAL COAT OF ALUMINOSILICATE ON THE SURFACE OF SILICA GEL

[75] Inventors: Zenji Hagiwara, Shiga; Masao Okubo, Hyogo, both of Japan

[73] Assignees: Hagiwara Research Corp.; Japan Electronic Materials Corporation, Japan

[21] Appl. No.: 662,040

[22] Filed: Feb. 28, 1991

[30] Foreign Application Priority Data

Feb. 28, 1990 [JP] Japan ................................. 2-47856

[51] Int. Cl.$^5$ ...................... A01N 25/26; A01N 59/16
[52] U.S. Cl. ................................. 424/409; 424/489; 424/618; 424/630; 424/641; 424/644; 424/650; 424/652; 424/653; 424/654; 424/655
[58] Field of Search ................ 428/403; 424/409, 404, 424/412, 413, 421, 489, 405

[56] References Cited

U.S. PATENT DOCUMENTS

| | | | |
|---|---|---|---|
| 1,920,492 | 8/1933 | Zellman | 424/618 |
| 3,159,536 | 12/1964 | Marotta | 424/421 |
| 4,929,431 | 5/1990 | Hagiwara et al. | 423/328 |
| 4,959,268 | 9/1990 | Hagiwara et al. | 428/403 |

FOREIGN PATENT DOCUMENTS 0116865  8/1984  European Pat. Off. .
0251783  1/1988  European Pat. Off. .

OTHER PUBLICATIONS
Copy of European Search Report for EP91-30-1660.

Primary Examiner—Thurman K. Page
Assistant Examiner—Neil Levy
Attorney, Agent, or Firm—Venable, Baetjer, Howard & Civiletti

[57] ABSTRACT

The present invention provides a novel antimicrobial composition and a process for preparing the composition which composition is useful as antimicrobial and/or bactericidal material. The antimicrobial composition of the invention comprises silica gel and an antimicrobial coat of aluminosilicate on the surface of the silica gel, said composition having a pore volume of at least 0.3 cm$^3$/g and a specific surface area of at least 100 m$^2$/g. The aluminosilicate coat consists of either partial or complete substitution of ion-exchangeable metal ion (M) in aluminosilicate solid particles represented by the formula $$xM_{2/n}O \cdot Al_2O_3 \cdot ySiO_2 \cdot zH_2O,$$

wherein x and y represent the numbers of molecules of the metal oxide and silicon dioxide, respectively, M is an ion-exchangeable metal, n is the atomic valence of M, and z is the number of molecules of water. One or more microbicidal metal ions selected from the group consisting of silver, copper, zinc, mercury, tin, lead, bismuth, cadmium and chromium are either partial or completely substituted for the ion-exchangeable metal ion (M).

2 Claims, No Drawings

SILICA-GEL BASED ANTIMICROBIAL COMPOSITION HAVING AN ANTIMICROBIAL COAT OF ALUMINOSILICATE ON THE SURFACE OF SILICA GEL

RELATED APPLICATION

The present application is closely related to copending application, Ser. No. 751,969 filed Aug. 29, 1991 pending entitled "Antimicrobial Compositions Having Resistance To Heat And Weathers"

BACKGROUND OF THE INVENTION

The present invention relates to a novel antimicrobial compound and a process for producing it. Furthermore, the present invention relates to a novel antimicrobial polymer composite comprising a polymer and the antimicrobial composition.

Inorganic aluminosilicates in which their alkali metal salt component is substituted by microbicidal metals have been known as antimicrobial compositions but antimicrobial compositions of the type contemplated by the present invention that are based on silica gel have not been known. In the conventional antimicrobial compositions based on aluminosilicates, microbicidal metals are uniformly distributed in their whole part including the surface and interior. In view of the structure of those compositions, not a large proportion of the microbicidal metals used is considered to work effectively in actual applications. Such being the case, the microbicidal metals have had to be used in large quantities in order to insure stronger antimicrobial activities. However, if antimicrobial compositions having high contents of microbicidal metals are added to polymers, they are discolored or stained.

It is also known to have a silver compound retained on a silica matrix through physical adsorption by treating the silica with a solution of silver nitrate. A problem with this method is that silver, being not chemically bound to the matrix, is labile and will be readily separated or released from the matrix.

The conventional aluminosilicate based antimicrobial compositions are commercially available in powder form comprising fine particles of 1-20 μm in size. In order to make them convenient for use in aqueous systems, the compositions must be formed into beads, pellets and other shapes that have increased mechanical strength and water resistance. In shaping the powder of conventional aluminosilicate based antimicrobial compositions, a special wet forming method is practiced using binders and other additives and the shaped part is then sintered at elevated temperatures to increase its strength. However, the thus shaped part of antimicrobial aluminosilicates (amorphous) or antimicrobial zeolites (crystalline) are not suitable for prolonged use in aqueous systems because if they are submerged in water, their water resistance deteriorates gradually and in an extreme case they are disintegrated to fines which are no longer effective for the intended purpose.

SUMMARY OF THE INVENTION

The present invention has been accomplished under these circumstances and has as an object providing a novel antimicrobial composition that is stable, that uses a smaller amount of microbicidal metals and that yet exhibits strong antimicrobial action.

Another object of the present invention is to provide a process for producing this novel antimicrobial composition.

A further object of the present invention is to provide an antimicrobial polymer composition using the novel antimicrobial composition.

The present inventors conducted intensive studies in order to solve the aforementioned problems of the prior art and found that they could be solved by providing the porous surface of silica gel with an antimicrobial coat of an aluminosilicate containing metal ions having microbicidal action. The present invention has been accomplished on the basis of this finding. The present inventors also found that an improved antimicrobial polymer composition could be obtained by dispersing said antimicrobial composition in a polymer.

DETAILED DESCRIPTION OF THE INVENTION

As is well known, silica gel is an amorphous porous material that is chiefly composed of $SiO_2$, represented by the general formula $(SiO_2)_x (H_2O)_y$, where x and y represent the numbers of molecules of $SiO_2$ and $H_2O$, respectively. Silica gel has long been used extensively as desiccants, adsorbents, catalyst carriers, and fillers in paper, rubber, plastics, etc. While silica gel is commercially available in granules, spherical beads or crushed products of various sizes, most of them have a $SiO_2$ content of at least 99.5%, with $Na_2O$, $Fe_2O_3$, $MgO$, $CaO$, $Al_2O_3$, etc. being present as impurities in very small amounts. The physical properties of commercially available silica gel vary with manufacturer, but most of the products currently sold in Japan have pHs in the range of 4-8, a true specific gravity of 2.2, pore volumes of 0.3-0.8 $cm^3/g$, specific surface areas of 100-800 $m^2/g$ (as measured by the BET method; unless otherwise noted, the values of specific surface area that appear hereinafter are those measured by the BET method), and pore sizes of 20-200 Å. Major sellers and manufacturers of silica gel in Japan are Fuji Davison Co., Ltd., Asahi Glass Co., Ltd., Mizusawa Industrial Chemicals, Ltd. and Toyota Chemical Industries, Ltd. A major overseas manufacturer of silica gel is Grace Chemicals, Co., which is producing silica gel beads of different sizes (10-30 μm; 0.5-1 mm; 1-3 mm) and physical data (pH in suspension =5-7). Silica gel products presently available from Grace Chemicals, Co. have pore volumes of 0.3-1.8 $cm^3/g$, specific surface areas of 20-750 $m^2/g$, and pore sizes of three different ranges, large, medium and small. Wide porous silica gels of XWP Series from Grace Chemicals, Co. have very large pore sizes ranging from 250 to 1,500 Å.

The silica gel to be used as the starting material in the present invention may be in the form of a powder, granules, beads or any other shaped parts. However, considering the case of performing a chemical treatment on silica gel by the method to be described below (i.e., treatment with an alkali solution and an aluminate solution), silica gel in a fine form is preferred. A more preferred type is porous silica gel in which a great number of capillary pores are present to provide large pore sizes and specific surface areas. For example, silica gel that is preferably used as the starting material in the present invention has a pore volume of at least 0.3 $cm^3/g$, and one having a void volume of at least 0.4 $cm^3/g$ is more preferred. The pore size of silica gel is preferably as large as possible, for example, at least 50 Å, more preferably at least 70 Å. The specific surface area of silica gel is at least 100 m²/g, more preferably at least 200 m²/g.

The silica gel material having these characteristics is preferred for the following reasons. First, silica gel having the physical data listed above is very porous and the capillary pores in it have a very active surface. If such silica gel is chemically treated by the method to be described hereinafter, whereby an aluminosilicate coat is formed on the active surfaces of capillary pores, and if microbicidal metals are retained on that coat in a stable way by ion exchange, chemical species and metal ions that take part in reaction will diffuse rapidly enough to permit the intended chemical reaction to proceed smoothly on the surfaces of pores in the silica gel. Further, as already mentioned, the microbicidal metal in the antimicrobial composition of the present invention is distributed substantially uniformly on the surfaces of pores in silica gel in a preferred way, so microbicidal metal ions formed as a result of dissociation will diffuse rapidly through pores to insure that those microbicidal metal ions contact bacteria or fungi over a sufficiently large area to inhibit their growth or kill them effectively.

Microbicidal metal ions may be any metal ions that effectively exhibit an antimicrobial and/or microbicidal action and such microbicidal metal ions are not limited to any particular kinds. Typical examples of microbicidal metal are silver, copper, zinc, mercury, tin, lead, bismuth, cadmium and chromium, and these metals may be used either on their own or as admixtures.

The aluminosilicate coat formed on the surface of the silica gel matrix in the present invention is generally represented by the following general formula:

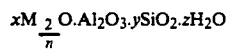

where x and y represent the numbers of molecules of the metal oxide and silicon dioxide, respectively; M is an ion-exchangeable metal; n is the atomic valence of M; and z is the number of molecules of water. M is usually a monovalent metal such as Li, Na or K and may sometimes be $NH_4^+$. If desired, such monovalent metals or $NH_4^+$ may be substituted either partially or totally with a divalent metal such as Mg, Ca, Sr, Ba, Mn, Ni, Co or Fe.

The coat made of the aluminosilicate may be either crystalline (zeolite) or amorphous or both (a combination of crystalline and amorphous phases). The thickness and composition of the aluminosilicate coat can be properly adjusted by controlling various factors such as the physical properties of silica gel used as the starting material, the amount of it use, alkali concentration, the amount of addition of a aluminate, reaction temperature and time. Irrespective of whether the aluminosilicate is crystalline or amorphous, the molar ratio of $SiO_2$ to $Al_2O_3$ is preferably within the range of 1.4–40. Typical examples of the aluminosilicate that can be used in the present invention include zeolite A having a $SiO_2$ to $Al_2O_3$ molar ratio of 1.4–2.4, zeolite X having a $SiO_2$ to $Al_2O_3$ molar ratio of 2–3, zeolite Y having a $SiO_2$ to $Al_2O_3$ ratio of 3–6, an amorphous aluminosilicate or a mixture of crystalline and amorphous aluminosilicate that have $SiO_2/Al_2O_3$ molar ratios of 1.4–30.

The process for producing the antimicrobial composition of the present invention is described below. Briefly stated, the antimicrobial composition of the present invention can be obtained by first chemically treating porous silica gel with an alkali solution and an aluminate solution and then forming an antimicrobial coat on the so treated surface of the silica gel.

The alkali solution may be a solution of an alkali metal hydroxide such as NaOH, KOH or LiOH, with the aqueous phase being held in an alkaline condition, for example, in a pH range of 9.5–12.5 during treatment. An example of the aluminate solution is a solution of an alkali metal aluminate such as $NaAlO_2$, $KAlO_2$, or $LiAlO_2$. The chemical treatment of silica gel with the alkali solution and the aluminate solution is performed at either ambient or elevated temperatures. As a result of this chemical treatment, $SiO_2$ present on the surfaces of capillary pores in silica gel undergoes reaction to have an aluminosilicate coat containing an ion-exchangeable metal formed on the active surfaces of pores. Subsequently, the coat is subjected to an antimicrobial treatment to prepare the antimicrobial composition of the present invention. For accelerating the microbicidal speed to insure excellent antimicrobial and/or microbicidal activity, the antibacterial composition of the present invention should have a pore volume of at least 0.3 cm³/g and a specific surface area of at least 100 m²/g.

After the chemical treatment, silica gel is washed with water to remove the excess alkali and metal component present in the solid phase. Washing with water may be performed by either a batch method or a column method. In the next step, silica gel is subjected to an ion-exchange treatment for allowing antimicrobial and-/or microbicidal metal ions to be retained on the aluminosilicate coat so that it becomes antimicrobial and/or microbicidal. To this end, silica gel is treated with a neutral or weakly acidic solution of salts containing one or more microbicidal metal ions selected from the group consisting of silver, copper, zinc, mercury, tin, lead, bismuth, cadmium and chromium. Useful examples of salts to be contained in the solution include: nitrates such as $AgNO_3$, $Cu(NO_3)_2$, $AgNO_3$ and $Zn(NO_3)_2$; sulfates such as $ZnSO_4$, $SnSO_4$ and $CuSO_4$-$SnSO_4$; perchlorates such as $AgClO_4$, $Cu(ClO_4)_2$, $Zn(ClO_4)_2$ and $Cd(ClO_4)_2$; chlorides such as $ZnCl_2$ and $ZnCl_2$-$CdCl_2$; and organic acid salts such as Ag-acetate, Zn-acetate, Cu-tartrate and Cd-citrate. One or more of these microbicidal metals are subjected to ion exchange at ambient or elevated temperatures with the ion-exchangeable metal (M) in the aluminosilicate coat, whereby a predetermined amount of the microbicidal metal or metals are supported stably in the coat by ionic bonding to provide it with a desired antimicrobial activity. In this way, the silica gel based antimicrobial composition of the present invention is prepared.

The solution containing one or more microbicidal salts to be used in the ion-exchange treatment may also contain metal ions having no antimicrobial activity. The degree by which the ion-exchangeable metal M in the aluminosilicate coat is substituted with microbicidal metal can be adjusted by controlling the concentration or composition of the salt solution containing the microbicidal metal, as well as the reaction temperature or time for ion exchange. By controlling the conditions for preparing the aluminosilicate coat and the conditions for ion exchange with the bactericidal metal ion, the total amount of microbicidal metals can be maintained at constant levels, say within the range of 0.003–0.5 mmol/100 m² (of the surface area of an anhydrous antimicrobial composition). Adjusting the characteristics of the microbicidal salt containing solution in the manner described above, the following advantage is obtained. That is, when microbicidal metal ions such as silver, copper and zinc in the antimicrobial and/or microbicidal aluminosilicate coat formed on the active surfaces of capillary pores in silica gel undergo hydrolysis, products such as oxides and basic salts are formed to contaminate the antimicrobial coat, whereby the inherent antimicrobial and/or microbicidal activity of the composition will deteriorate. However, this problem can be avoided by proper adjustment of the microbicidal salt containing solution. In place of performing ion exchange using the microbicidal metal ion containing solution, organic solvents such as alcohols and esters, or mixtures of solvents and water may be used to perform the intended ion exchange. For instance, if an alcoholic solvent such as methyl alcohol or ethyl alcohol is used in substituting the ion-exchangeable metal M in the aluminosilicate coat with $Sn^{2+}$ which is a highly hydrolyzable microbicidal metal ion, precipitation of SnO, $SnO_2$, basic tin compounds, etc. on the coat can be prevented to insure that the antimicrobial activity of the coat will not deteriorate.

After the treatments described above, silica gel is washed with water until no microbicidal metal ions are detected in the filtrate. Thereafter, silica gel is dried at 100°–110° C. to complete the process of preparing the antimicrobial composition of the present invention. If a specific use of the compound needs further reduction in the water content, it may be dried under vacuum or dehydration may be performed with the heating temperature elevated to 200°–350° C.

To achieve excellent antimicrobial and/or microbicidal activity against bacteria and fungi or to insure anti-algal effect, the total content of microbicidal metals in the antimicrobial composition of the present invention is preferably at least 0.003 mmol/100 $m^2$ (of the surface area of the composition in anhydrous state), more preferably at least 0.005 mmol/100 $m^2$. Usually, the range of 0.03–0.5 mmol/100 $m^2$ will suffice. If two or more microbicidal metals are used, their sum is preferably within the ranges set forth above. The term "anhydrous" state means a state being free from crystal water, i.e., a state that $Z=0$ in a formula such as

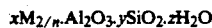
$xM_{2/n}\cdot Al_2O_3\cdot ySiO_2\cdot zH_2O$

The present invention also provides an antimicrobial polymer composition that is chiefly composed of a polymer and the antimicrobial composition described above. A detailed discussion of this polymer composition is given below.

Both halogenated and non-halogenated organic polymers may be used in preparing the antimicrobial polymer composition of the present invention. Non-halogenated organic polymers may be synthetic or semi-synthetic and include, but not limited to, the following:

Thermoplastic synthetic polymers such as polyethylene, polypropylene, polystyrene, polyamide, polyesters, polyvinyl alcohol, polycarbonates, polyacetals, ABS resins, acrylic resins, fluorine resins, polyurethane elastomers and polyester elastomers; thermosetting synthetic polymers such as phenolic resins, urea resins, melamine resins, unsaturated polyester resins, epoxy resins and urethane resins; and regenerated or semi-synthetic polymers such as rayon, cuprammonium rayon, cellulose monoacetate, cellulose diacetate and cellulose triacetate. If a strong antimicrobial and/or microbicidal effect is necessary, the polymer composition is preferably foamed or otherwise shaped into a net, a fiber, etc. Preferred from this viewpoint are organic or fiber-forming polymers such as synthetic polymers exemplified by nylon 6, nylon 66, polyvinyl alcohol, polyethylene terephthalate, polybutylene terephthalate, polyacrylonitrile, polyethylene, polypropylene and copolymers thereof, and regenerated or semi-synthetic polymers exemplified by rayon, cuprammonium rayon, cellulose monoacetate, cellulose diacetate and cellulose triacetate. Halogenated organic polymers that can be used in the present invention also are not limited to any particular kinds and may be exemplified by polyvinyl chloride and polyvinylidene chloride.

The time at which the silica gel based antimicrobial composition is added to the polymer and the method by which it is added are not limited in any particular way in the present invention. For example, the antimicrobial composition may be mixed with a starting monomer and the mixture is then polymerized. In another method, the composition may be mixed with a reaction intermediate and the mixture is then polymerized. Alternatively, the composition may be mixed with the completed polymer, if desired, the silica gel based antimicrobial is mixed with polymer pellets or a master batch is prepared from a polymer containing said composition and the mixture or master batch is shaped to a desired form. In still another method, the antimicrobial composition is mixed with a molding dope, for example, a spinning solution. The procedure of these methods is hereinafter referred to simply as "mixing the silica gel based antimicrobial composition with a polymer of adding it to the polymer". A suitable method may be adopted taking into account the characteristics of the polymer used and process conditions. In ordinary cases, the silica gel based composition is desirably mixed with the polymer just before molding. However, in order to insure more efficient dispersion of the silica gel based antimicrobial composition, it may be mixed with a monomer. Prior to addition to a polymer, the antimicrobial composition may advantageously be dried or heat-treated as already mentioned hereinabove. When a predetermined amount of the antimicrobial composition is to be added to a polymer, the atmosphere (e.g. an oxidizing atmosphere such as the air or an inert gas atmosphere such as $N_2$ or $CO_2$), the temperature for mixing or the mixing time may be held at preferred conditions in accordance with the specific characteristics of the polymer used. The silica gel based antimicrobial composition is preferably used in an amount of 0.01–20 wt % of the total weight of the polymer composition. If the content of the silica gel based composition is less than 0.01 wt % of the total weight of the polymer composition, the antimicrobial and/or microbicidal activity of the polymer composition is often unsatisfactory against common bacteria and fungi. If the content of the silica gel based composition is more that 20 wt % of the total weight of the polymer composition, the antimicrobial and/or microbicidal activity of the resulting polymer composition is saturated and any further addition of the silica gel based composition will not contribute to an improved antimicrobial and/or microbicidal action. Furthermore, excessive addition of the silica gel based composition has the potential to deteriorate the physical properties of the finally obtained polymer compsition.

The particle size of the silica gel based antimicrobial composition that is advantageously used to produce the antimicrobial polymer composition of the present invention is discussed below. While there is no particular limitation on the particle size of said composition, there is of course a preferred range depending on the specific use of the final product. For example, particles of the antimicrobial composition with sizes of 30-100 mesh can be used for mixing with the polymer but in order to insure more uniform dispersion in the polymer, smaller particles, for example, those having sizes of 200-300 mesh or much finer particles with sizes of from several microns to less than a hundred microns, may be used.

The particle size of the antimicrobial composition may be adjusted by selecting the particle size of the starting silica gel or by pulverizing the prepared silica gel based antimicrobial composition with a mill that is selected as appropriate for a specific purpose. When the antimicrobial polymer composition of the present invention is a shaped part having a certain thickness, for example, in the case where it is to be applied to various types of containers, pipes, granules of filaments of large denier, the silica gel based antimicrobial composition may have particle sizes of up to less than a hundred to less than a thousand microns or even more. If, on the other hand, the polymer composition is to be shaped into fibers of fine denier or thin films, the particle size of the silica gel based antimicrobial composition is desirably small. For example, in the case of manufacturing fibers for apparel, particle sizes of not more than 6 microns are preferred.

In addition to the silica gel based antimicrobial composition, the antimicrobial polymer composition of the present invention may contain other ingredients that are commonly used in the art. Examples of such secondary ingredients include: polymerization catalysts, stabilizers, weathering (lightfast) agents, compounding agents, antioxidants, activators, matting agents, foaming agents, flame retardants, modifiers, brighteners, pigments (colorants), inorganic or organic fillers, various plasticizers, and lubricants. These additives may be incorporated as required. The antibacterial polymer composition of the present invention may also contain liquids or organic solvents. When said composition is to be used as a shaped part, its shape and size are in no way limited. In order to provide the shaped part with an antimicrobial and/or microbicidal activity, it may be imparted to the whole part of the polymer, or if desired, to only part thereof. When the microbicidal polymer composition of the present invention is shaped part, its microbicidal action is considered to be largely dependent on the silica gel based antimicrobial composition present near the surface of the shaped part, so it may be advisable to provide the shaped part with a multilayer structure and treat its outer layer to acquire a microbicidal activity. In the case of fibers, a core/sheath yarn may be prepared by a known conjugate fiber spinning technique, with the antimicrobial polymer composition of the present invention being used as the sheath component.

The present invention further provides an antimicrobial composition for use in aqueous systems that comprised silica gel having on its surface a coat of aluminosilicate containing at least one microbicidal metal ion selected from the group consisting of silver and zinc. This antimicrobial composition has been proposed with a view to improving the known microbicides for use in aqueous systems. This antimicrobial composition has the following two major advantages: there is no particular need to shape this composition in the manner described in connection with the antimicrobial zeolite; it can be easily shaped in granules of various sizes (large, medium and small) spherical beads and other forms by selecting the shape of the starting silica gel in accordance with a specific object. Further, the antimicrobial composition of the present invention for use in aqueous systems has by far greater mechanical strength and water resistance than the shaped part of known antimicrobial zeolites, and it will not readily disintegrate into fine particles in water and hence withstand prolonged use in aqueous systems. As a further advantage, the antimicrobial and/or microbicidal activity of this composition against bacteria and fungi is remarkable and it is capable of inhibiting or killing microorganisms in a shorter time than known antimicrobial zeolites. In other words, the microbicidal speed of the composition is surprisingly high.

If the composition contains silver as the sole microbicidal metal, its total content is preferably at least 0.0003 mmol, more preferably at least 0.005 mmol, per 100 $m^2$ of the surface area of the composition in anhydrous state in order to insure that the composition will exhibit strong antimicrobial and/or microbicidal action against bacteria and fungi, as well as good antialgal effect. If the composition contains both silver and zinc as microbicidal metals, the total contents of silver and zinc are preferably at least 0.0002 mmol and 0.02 mmol, respectively, per 100 $m^2$ of the surface area of the composition in anhydrous state. If the composition contains zinc as the sole microbicidal metal, its total content is preferably at least 0.08 mmol per 100 $m^2$ of the surface area of the composition in anhydrous state. In order to insure that the antimicrobial composition of the present invention will exhibit satisfactory antimicrobial and/or microbicidal effect in water over a prolonged time, a predetermined amount of the composition may be used after the content of a microbicidal metal of interest is adjusted to a value not less than its lower limit specified above in accordance with the quality of water to be treated with that composition. In performing antimicrobial and/or microbicidal treatment on ordinary aqueous systems, the composition in which the total content of microbicidal metal is adjusted to lie within the range of 0.0002-0.5 mmol per 100 $m^2$ of the surface area of the composition in anhydrous state may be added in the necessary amount as appropriate for the quality of water to be treated.

The antimicrobial composition of the present invention for use in aqueous systems preferably has a pore volume of at least 0.3 $cm^3/g$ and a specific surface area of at least 100 $m^2/g$ in order to insure that said composition exhibits satisfactory microbicidal action at an increased speed.

The silica gel based antimicrobial composition of the present invention and the antimicrobial polymer composition which uses it have the following features and advantages.

First, silica gel used as the matrix of the antimicrobial composition is porous and the pores in it have an active surface. Hence, chemical species and metal ions will diffuse rapidly during the formation of an aluminosilicate coat and ion exchange, whereby the intended chemical reaction will proceed smoothly to facilitate the production of an antimicrobial composition having desired performance.

The pores in the silica gel based antimicrobial composition of the present invention are larger than those in known aluminosilicate based antimicrobial agents. Hence, microbicidal metal ions formed as a result of dissociation of the composition will readily diffuse through the pores to have easy access to microorganisms. On the other hand, the pores in known aluminosilicate based antimicrobial compositions, such as antimicrobial zeolites, are so small in size that microbicidal metal ions formed as a result of dissociation will diffuse very slowly and sometimes fail to have contact with microorganisms. Hence even if the apparent specific surface area is increased by using porous aluminosilicate particles, the area over which a microbicidal metal makes effective contact with microorganisms will not increase so much as to enhance their antimicrobial performance to a desired level. This is because the effectiveness of the microbicidal metal present on the surface of the matrix is reduced by "dead spaces" where it is unable to have contact with microorganisms.

The antimicrobial composition of the present invention does not have this problem and all microbicidal metals that are present on the surface of the matrix work effectively by contacting microorganisms.

Further, the silica gel matrix is covered with an aluminosilicate substituted by a microbicidal metal, so the amount of "wasted" microbicidal metal which is occluded within the matrix and hence prevented from contact with microorganisms is substantially reduced.

Because of these two factors, the "effective availability" of the microbicidal metal, namely, the proportion of the metal used that is occupied by the metal present on the surface, is markedly increased to insure that the composition of the present invention need be used in a smaller amount to exhibit satisfactory antimicrobial performance.

Hence, this composition can be mixed with a polymer to produce an effective antimicrobial polymer composition without causing staining or discoloration which would otherwise occur if a microbicidal metal is used in a large amount.

The antimicrobial composition of the present invention has the following additional features or advantages.

(1) It is totally composed of inorganic components and the microbicidal metal in it is stably held on the matrix by ionic bonding. Even if the composition is added or mixed with a polymer, the release or separation of the microbicidal metal is negligible. Hence, the antimicrobial polymer based on this composition has the advantage that its antimicrobial effect will be sustained for a longer period than that exhibited by polymers containing organic antimicrobial agents. Needless, the evaporation loss of the particles in the polymer is nil.

(2) The antimicrobial composition of the present invention has no toxicity, is highly safe to the human body and can be handled with great ease.

(3) The antimicrobial composition to be used in the present invention can not only be added and mixed with various polymers in an easy way but it can also be dispersed uniformly to provide a homogeneous polymer composition.

(4) The antimicrobial composition has a stable structure and its heat resisting and weathering properties are excellent. When this composition is used to prepare a microbicidal polymer, its presence will neither deteriorate the physical properties of the polymer nor does it adversely affect the heat resistance or weatherability of the polymer composition.

(5) The antimicrobial composition of the present invention has a broad antimicrobial spectrum and proves effective against many bacterial and fungi. It is also anticipated to work as an antialgal agent.

(6) Commercial products of synthetic zeolites contain free alkalies in significant amounts (pH in 1 g of an aqueous suspension=11.5-12). Antimicrobial zeolites are prepared from these materials by ion exchange. In this case, the free alkalies in the starting zeolite will cause extensive adverse effects on the quality of the antimicrobial zeolite. Thus, it is necessary to adopt an additional step of removing the free alkalies from zeolite. In contrast, the preparation of the antimicrobial composition to be used in the present invention involves a treatment in a weakly alkaline range as already mentioned above, so there is no particular need to remove excess alkali. In other words, alkalies do not present any problem in the preparation of the composition of the present invention and the finally obtained composition is free from alkalies.

(7) The antimicrobial composition to be used in the present invention is based on silica gel, so when it is added to or mixed with a polymer, it exhibits not only antimicrobial and/or microbicidal effect but also the inherent action of silica gel as a filler.

(8) The antimicrobial composition of the present invention is useful for the purpose of providing antimicrobial property for paints, pigments, paper, rubber, etc. Further, the composition has the potential to be used for the purpose of providing antimicrobial and/or microbicidal property for various coatings, and for the purpose of providing antimicrobial property for construction materials such as joint fillers, wall materials and tiles. Another potential application of the composition is in water treatment.

(9) According to the present invention, polymer compositions can be rendered partially or totally resistant to microorganisms. Further, such antimicrobial polymer compositions have the ability to provide antimicrobial and/or microbicidal property for the atmosphere (gas or liquid phase) with which they make contact.

(10) The antimicrobial polymer composition of the present invention also has the potential to be used in applications where deodoring, dehumidification and keeping of freshness are required.

(11) The present invention can be utilized to provide antimicrobial and/or microbicidal property to various polymers including halogenated and non-halogenated organic polymers. The antimicrobial composition of the present invention could be used not only for the purpose of providing antimicrobial property for various waxes, paints, pigments, papers, adhesives, coatings and construction materials (e.g. joint fillers, wall materials and tiles) but also in water treatment. The antimicrobial composition of the present invention can also be used to provide antimicrobial property for polymer jackets on optical fibers.

(12) The antimicrobial composition of the present invention for use in aqueous systems has high water and wear resistance. Even if it is used in water, it remains intact for a long time, with only negligible disintegration into fines.

(13) When the antimicrobial composition of the present invention is used in water for microbicidal purposes, the microbicidal metal present in pores in silica gel exhibit a very high availability (i.e. the composition has a higher efficiency of utilization than known antimicrobial zeolites).

(14) The antimicrobial composition of the present invention for use in aqueous system is effective not only against common bacterial and fungi but also against algae.

The following examples are provided for the purpose of further illustrating the present invention but are in no way to be taken as limiting.

EXAMPLE 1

This example relates to the preparation of an antimicrobial composition according to the present invention that uses silica gel as a matrix and that contains silver as a microbicidal metal.

Three liters of desalted water was added to ca. 1.4 kg of crushed silica gel (product of Nishio Kogyo K.K.; specific surface area, 450 m$^2$/g; pore size, 75 Å; pore volume, 0.8 ml/g; particle size, 50-80 mesh). The mixture was stirred at 450-500 rpm to form a homogenous slurry. To the slurry, a 0.5N solution of sodium hydroxide was added slowly until the pH of the slurry was finally adjusted to 9.5-10.0. Then, ca. 63 g of NaAlO$_2$ dissolved in 3 l of water was added to the slurry and the mixture was stirred at 20°-30° C. for ca. 12 hours at 450-500 rpm. After stirring, the mixture was filtered and the solid phase was washed with water to remove excess alkali and unreacted NaAlO$_2$. During the washing, the pH of the filtrate was held at about 9. To the solid phase, a solution of silver nitrate (aq. sol. containing ca. 0.68M AgNO$_3$) was added and the resulting mixture was stirred continuously at 450-550 rpm over a period of about 7 hours. During the stirring, the mixture was held at room temperature (20°-21° C.). The above procedure substantially completed the preparation of an antimicrobial composition containing microbicidal silver ions. After the end of the reaction, the product was filtered and washed to remove excess Ag$^+$ from the solid phase. The washed product was dried at 100°-110° C. to obtain a silica gel based antimicrobial composition containing silver as a microbicidal metal.

The antimicrobial composition of the present invention prepared in Example 1 had a specific surface area of 324 m$^2$/g (as measured by N$_2$ gas adsorption in the BET method) and a pore volume of 0.72 cm$^3$/g. The amount of silver as determined was 4.90% (on an anhydrous basis). The composition contained 0.14 mmol of silver per 100 m$^2$ of the surface area on an anhydrous basis.

TABLE 1

| Antimicrobial Composition (Example 1) | |
|---|---|
| Specific surface area (m$^2$/g) | Microbicidal metal (Ag) in mmol/100 m$^2$ |
| 324 | 0.14 |

EXAMPLE 2

This example relates to the preparation of an antimicrobial composition according to the present invention that uses silica gel as a matrix and that contains both silver and zinc as microbicidal metals.

Desalted water (2.5 l) was added to ca. 1.3 kg of spherical silica gel beads (product of Toyota K.K.; specific surface area, 450 m$^2$/g; pore size, 60 Å; pore volume, 0.75 cm$^3$/g; particle size; 40 mesh pass). The mixture was stirred at 400-450 rpm to form a homogeneous slurry. To the slurry, a 0.5N solution of sodium hydroxide was added slowly until the pH of the slurry was finally adjusted to 9.5-10.0. Then, ca. 2.6 l of an aqueous solution of sodium aluminate (0.27 mol/l) was added to the slurry, which was stirred at 20°-23° C. for ca. 15 hours at 450-500 rpm to form an aluminosilicate coat on the surfaces of pores in the silica gel. Subsequently, the mixture was filtered and the solid phase was washed with water to remove excess alkali and unreacted sodium aluminate. During the washing, the pH of the filtrate was held at ca. 9. A mixture of AgNO$_3$ and Zn(NO$_3$)$_2$ (an aqueous solution of 0.6M AgNO$_3$ and 0.2M Zn(NO$_3$)$_2$; pH=4.1) was added to the washed solid phase and the resulting mixture was held at 20°-21° C. and stirred continuously at 450-500 rpm over a period of ca. 15 hours. By the above procedure of ion exchange reaction, an antimicrobial composition containing silver and zinc as microbicidal metals was prepared. The composition was filtered and washed to remove excess silver and zinc from the solid phase. The washed product was dried at 100°-110° C. to prepare a silica gel based antimicrobial composition containing both silver and zinc as microbicidal metals.

The antimicrobial composition of the present invention prepared in Example 2 had a specific surface area of 319 m$^2$/g (as measured by N$_2$ gas adsorption in the BET method) and a pore volume of 0.67 cm$^3$/g. The amounts of silver and zinc as determined were 3.79% and 0.83% (on an anhydrous basis). The composition contained silver and zinc in amounts of 0.11 mmol and 0.04 mmol, respectively, per 100 m$^2$ of the surface area on an anhydrous basis.

TABLE 2

| Antimicrobial Composition (Example 2) | | |
|---|---|---|
| Specific surface area (m$^2$/g) | Microbicidal metal in mmol/100 m$^2$ | |
| | Ag | Zn |
| 319 | 0.11 | 0.04 |

In order to compare the antimicrobial activity of the composition prepared in Example 2 with that of a known antimicrobial zeolite, a test was conducted under the same conditions according to the "shake flask method" reviewed by the Fibrous Product Sanitary Processing Conference". In the test, *Escherichia coli* and *Staphylococcus aureus* were used as test bacteria. The antimicrobial zeolite used as a comparative sample was dried fine powder of NaAgZnZ (3.97% Ag and 1.27% Zn on an anhydrous basis; Z=the matrix of zeolite A). The test procedure was as follows.

(a) A suspension (1/15M; pH 7.2) containing ca. 10$^8$ cells/ml of a test bacterium was prepared and diluted appropriately for the test.

(b) Test by the shake flask method: The test sample (the dried powder of known antimicrobial zeolite or the antimicrobial composition of Example 2) was taken in an amount of 0.005 g into a 200-ml volumetric flask. A phosphate buffer solution and the suspension of test bacterium were added to make a total volume of 50 ml, with the number of cells being adjusted to 10$^6$ per ml.

(c) Test bacteria: *Escherichia coli* (IFO-12734) and *Staphylococcus aureus* (IFO-12732)

(d) Medium: Mueller Hinton 2 (BBL)

The test results are shown in tables 3 and 4 below, in which the data for a control containing no antimicrobial agent is also shown.

TABLE 3

Comparison of Antimicrobial Activity Between Antimicrobial Zeolite and the Antimicrobial Composition of Example 2 (Test bacterium: E. coli; Initial cell count: $5.6 \times 10^6$/ml; total liquid volume: 50 ml)

| Antimicrobial agent | | Antimicrobial metal content | No. of viable cells per ml | | |
|---|---|---|---|---|---|
| Type | Amount | | 0 | 10 | 30 (min) |
| Antimicrobial zeolite (NaAgZnZ) | 5 mg/50 ml (0.1 mg/ml) | Ag = 0.20 mg Zn = 0.06 mg | $5.6 \times 10^6$ | $1.1 \times 10^6$ | 0 |
| Antimicrobial composition of Example 2 | 5 mg/50 ml (0.1 mg/ml) | Ag = 0.19 mg Zn = 0.04 mg | $5.6 \times 10^6$ | $8.9 \times 10^3$ | 0 |
| Control | No Antimicrobial agent added | | $5.6 \times 10^6$ | $5.4 \times 10^6$ | $5.2 \times 10^6$ |

TABLE 4

Comparison of Antimicrobial Activity Between Antimicrobial Zeolite and the Antimicrobial Composition of Example 2 (Test bacterium: Staphyl. aureus; Initial cell count: $1.5 \times 10^6$/ml; Total liquid volume: 50 ml)

| Antimicrobial agent | | Antimicrobial metal content | No of viable cells per ml | | | | | |
|---|---|---|---|---|---|---|---|---|
| Type | Amount | | 0 | 5 | 10 | 15 | 30 | 120 (min) |
| Antimicrobial zeolite (NaAgZnZ) | 5 mg/50 ml (0.1 mg/ml) | Ag = 0.20 mg Zn = 0.06 mg | $1.5 \times 10^6$ | — | — | — | $6.8 \times 10^6$ | 0 |
| Antimicrobial composition of Example 2 | 5 mg/50 ml (0.1 mg/ml) | Ag = 0.19 mg Zn = 0.04 mg | $1.5 \times 10^6$ | $4.1 \times 10^3$ | $5.2 \times 10$ | 0 | 0 | 0 |
| Control | No antimicrobial agent added | | $1.5 \times 10^6$ | $1.2 \times 10^6$ | $1.3 \times 10^6$ | $1.2 \times 10^6$ | $1.3 \times 10^6$ | $1.2 \times 10^6$ |

Each of the antimicrobial zeolite and the antimicrobial composition of Example 2 which were subjected to the antimicrobial activity test under discussion contained both silver and zinc as microbicidal metals and the former contained these metals in slightly larger amounts than the latter. However, as Table 3 shows, the antimicrobial composition of the present invention exhibited greater antimicrobial activity against *Escherichia coli* in view of the high rate at which the number of cells decreased with time. After the passage of 10 minutes, the cell count in the suspension containing the antimicrobial zeolite was $1.1 \times 10^6$ per ml (death rate, 80.36%) but the number of viable cells in the suspension containing the antimicrobial composition of Example 2 decreased to a much smaller level of $8.9 \times 10^3$/ml (death rate, 99.84%).

In the test using *Staphylococcus aureus* (see Table 4), the number of viable cells in the suspension containing antimicrobial zeolite was $6.8 \times 10^4$/ml after the passage of 30 minutes and the death rate was 95.47%. On the other hand, the viable cell count in the suspension containing the antimicrobial composition of Example 2 was $5.2 \times 10$/ml at 10 minutes and almost all cells had been killed. After the passage of 15 minutes, the death rate was 100%. Table 4 clearly shows that the attenuation rate of *Staphylococcus aureus* was by far faster when the antimicrobial composition of the present invention than when the known antimicrobial zeolite was used.

The results of the antimicrobial activity test revealed that the antimicrobial composition of the present invention is superior to the known antimicrobial zeolite in antimicrobial action. This is an important point worth particular mention. The difference between the two antimicrobial agents in antimicrobial and/or microbicidal effect would originate from their essential structural difference. The antimicrobial composition of the present invention has a silicon-oxgen skeletal structure based on amorphous silica gel whereas the known antimicrobial zeolite is crystalline and has a silicon-oxygen-aluminum skeletal structure. Because of this obvious structural difference, the two antimicrobial agents will unavoidably differ in physical properties. For example, both agents are porous but the size of pores in the matrix is much greater in the antimicrobial composition of the present invention than in the antimicrobial zeolite. There is another difference and that is in the distribution of bactericidal metals. In the composition of the present invention, microbicidal metals are distributed on the surface of pores, substantially by ionic bonding. On the other hand, in the known antimicrobial zeolite, microbicidal metals are distributed uniformly in the zeolite matrix. When this structural difference is taken into account together with the arrival of microorganisms through diffusion at the active sites where microbicidal metals are coordinated and the area of contact between the microorganism and microbicidal metal, the composition of the present invention is by far advantageous over the known antimicrobial zeolite. In addition, the efficiency of utilization of microbicidal metals for antimicrobial and/or microbicidal purposes is higher in the composition of the present invention than in the known antimicrobial zeolite. The pores present in the matrix of the known antimicrobial zeolite have such a small size that depending on the kind of microorganisms, the diffusion rate will decrease. Further, microbicidal metal ions formed as a result of dissociation will diffuse so slowly that an unduly long time is taken for those metal ions to contact microorganisms or, in an extreme case, such contact is entirely impossible. These phenomena will contribute to a lower efficiency of utilization of microbicidal metals in the antimicrobial zeolite.

EXAMPLE 3

This example relates to the preparation of an antimicrobial composition according to the present invention that uses silica gel as a matrix and that contains copper as a microbicidal metal.

Desalted water (1.7 l) was added to ca. 0.9 kg of silica gel (ID silica gel of Nishio Kogyo K.K.; specific surface area, 310 m²/g; pore size, 150 Å; pore volume, 1.2 ml/g; particle size, 50–80 mesh). The mixture was stirred at 450–500 rpm to form a homogeneous slurry. To the slurry, a 0.5N sodium hydroxide solution was slowly added until the pH of the slurry was finally adjusted to 9.5–10.0. Then, an aqueous solution of sodium aluminate prepared by dissolving ca. 100 g of NaAlO₂ in 1.8 l of water was added to the slurry, which was stirred at 30°–32° C. for ca. 16 hours at 450–500 rpm. After these treatments, the silica gel was packed in an ion-exchange column having an inside diameter of 50 mm and washed with water at a flow rate of 4–5 ml/min to remove excess alkali and unreacted NaAlO$_2$, with the pH of the effluent from the washed column being held at 9. Subsequently, the packing in the column was treated with an excess aqueous solution of cupric nitrate (pH 4.0). Stated more specifically, the column packing was treated with an aqueous solution of Cu(NO$_3$)$_2$ containing 2.5–3 equivalents of Na$^+$ in the NaAlO$_2$ solution. The liquid temperature was 20°–22° C. and the flow rate was 3–4 ml/min. After the ion exchange, the column packing was washed with water at a flow rate of 4–5 ml/min to remove excess Cu$^{2+}$ from the solid phase. After the washing, the column packing was recovered and dried at 100°–110° C. to prepare a silica gel based antimicrobial composition containing copper as a microbicidal metal.

The antimicrobial composition of the present invention prepared in Example 3 had a specific surface area of 248 m$^2$/g (as measured by N$_2$ gas adsorption in the BET method) and a pore volume of 1.04 cm$^3$/g. The amount of copper as determined was 4.25% (on an anhydrous basis). The composition contained copper in an amount of 0.27 mmol per 100 m$^2$ of the surface area on an anhydrous basis.

TABLE 5

| Antimicrobial Composition (Example 3) | |
|---|---|
| Specific surface area (m$^2$/g) | Microbicidal metal (Cu) in mmol/100 m$^2$ |
| 248 | 0.27 |

The antimicrobial power of the silica gel based compositions of the present invention is discussed below.

Inhibition Zone Formation Test

An inhibition zone formation test was conducted by the method summarized below.

(1) The test sample (the dried product of the antimicrobial composition prepared in Example 1 or 2) was suspended at a concentration of 100 mg/ml and impregnated in a disk.

(2) For the growth of bacteria, a Mueller Hinton medium was used, and for the growth of fungi, a Sabouraud's agar medium was used.

(3) The test microorganism was suspended in physiological saline at a concentration of 10$^8$ cells/ml and 0.1 ml of the suspension was dispersed in the media with a Conradi's rod.

(4) The disk impregnated with the test sample was plated on the media.

(5) As for the bacteria. the disks were checked for the formation of an inhibition zone after the passage of 18 hours at 37° C. As for the fungi, the disks were checked for the formation of an inhibition zone after the passage of one week at 30° C. The results are shown in Table 6 below.

TABLE 6

| | Evaluation of Antimicrobial Activity (Inhibition Zone Formation) | | |
|---|---|---|---|
| Antimicrobial composition Microorganism | Example 1 | Example 2 | Silica Gel (starting material used in Example 1 |
| Eschirichia coli | + | + | − |
| Staphylococcus aureus | + | + | − |
| Pseudomonas aeruginosa | + | + | − |
| Aspergillus flavus | + | + | − |
| Aspergilus niger | + | + | − |

+: Inhibition zone formed
−: No Inhibition zone formed

The antimicrobial composition prepared in Example 1 which contained Ag as a microbicidal metal and the antimicrobial composition prepared in Example 2 which contained both Ag and Zn as microbicidal metals were effective against both bacterial *Escherichia coli*, *Staphylococcus aureus* and *Pseudomonas aeruginosa* and fungal *Asperigillus flavus* and *Aspergillus niger*, forming an inhibition zone in all of these five cases. The "silica gel" mentioned in Table 6 was the silica gel used as the starting material in the preparation of the antimicrobial composition in Example 1. Having no antimicrobial activity, this silica gel did not form any inhibition zone as indicated in Table 6.

Death Rate Measurement

One milliliter of a suspension containing 10$^5$/ml of spores of *Aspergillus niger* or *Aspergillus flavus* was injected and mixed with 9 ml of a suspension of the test sample (the dried product of the antimicrobial composition prepared in Example 1, 2 or 3) at a concentration of 500 mg/ml and the mixture was left to stand at 30° C. for 24 hours. A portion (0.1 ml) of the mixture was dispersed in a Sabouraud's agar medium and cultured at 30° C. for 48 hours. The number of viable cells was counted to determine the death rate of each fungus. The results are shown in Table 7.

TABLE 7

| | Measurement of Death Rate | |
|---|---|---|
| Antimicrobial composition | Death Rate (%) | |
| | Aspergillus flavus | Aspergillus niger |
| Example - 1 | 100 | 100 |
| Example - 2 | 100 | 100 |
| Example - 3 | 96 | 81 |

The antimicrobial compositions prepared in Examples 1 and 2 had a 100% death rate for *Aspergillus flavus* and *Aspergillus niger*, indicating the strong fungicidal action of the compositions. The antimicrobial composition prepared in Example 3 also had good antifungal effect as already demonstrated in Example 3.

Method of Testing Antimicrobial Activity in Examples 4–8 and Comparative Example Additional samples were prepared in Examples 4–8 and Comparative Example and their performance was evaluated by an antimicrobial activity test in the manner to be described below. When the test samples were shaped in a plate, film or sheet form, the test was conducted by spraying, whereas the samples in the form of monofilaments were tested by the "shake flask method"

specified by the Fibrous Product Sanitary Processing Conference.

(I) Preparation of a cell suspension of bacterium:

The cells of a test bacterium that had been cultivated in a common agar medium at 37° C. for 18 hours were suspended in a phosphate buffer (1/15M; pH 7.2) at a concentration of $10^8$ cells/ml and diluted as appropriate for the test.

(II) Preparation of a cell suspension of fungus:

Conidia of a test fungus that had been cultivated on a slant potato dextrose agar medium at 25° C. for 7 days were suspended in physiological saline containing sterile 0.05% polysorbate to prepare a suspension at a concentration of $10^7$ cells/ml, which was diluted as appropriate for the test.

(III) Antimicrobial activity test by the spray method:

The surface of a test piece (50×50×ca. 1.5 mm except for a film which was 30 μm thick) cleaned with alcohol-impregnated absorbent wadding was sprayed with a predetermined amount of cell suspension and stored at 35° C. for a predetermined time. Before measurement, the cells on the test piece were washed off and the number of cells in the washings was counted.

(IV) Antimicrobial activity test by the shake flask method:

One gram of a test piece (monofilament) was put into a 200-ml volumetric conical flask containing 70 ml of a phosphate buffer. The flask was further charged with a suspension of test microorganism at a concentration of $10^4$ cells/ml and shaken at 25°±5° C. and the number of viable cells was counted at given time intervals.

(V) Test microorganism:
Staphylococcus aureus IFO-12732
Escherichia coli IFO-12734
Aspergillus niger IFO-31125

(VI) Medium (for counting viable cells): Muller hinton 2 (BBL) for bacteria, and Sobouraud's dextrose agar (BBL) for fungus

EXAMPLE 4

This example relates to the preparation of a shaped part of polyvinylidene chloride (PVDC) containing an antibacterial composition having silver supported as a microbicidal metal, as well as the evaluation of its antimicrobial activity.

The dried product of the antimicrobial composition containing silver as a microbicidal metal which was prepared in Example 1 (Ag=0.14 mmol per 100 m²/g of the surface area in anhydrous state; specific surface area, 324 m²/g as measured by $N_2$ adsorption in the BET method) was ground into fine particles and heated at 190°–200° C. under vacuum to a water content of 2% and below. The dried fine particles were mixed with PVDC, with the former being in an amount of 1.5% or 3%. The mixtures were then heated close to 180° C., homogenized at the same temperature, and pressed at ca. 20 kg/cm².G to form parts measuring ca. 100×100×1.5 mm. Each of the shaped parts was cut into small test pieces (ca. 50×50×1.5 mm). The thus prepared test pieces were designated PVDC-1 and PVDC-2. As a comparison, a shaped part of PVDC (ca. 100×100×1.5 mm) containing no antimicrobial composition was prepared for use in a blank test. This was cut into small test pieces (PVDC-BL; ca. 50×50×1.5 mm). All of the test pieces were subjected to an antimicrobial activity test by the spray method and the results were as shown in Table 8.

TABLE 8

Antimicrobial Activity Test by the Spray Method (Example 4)

| Test sample | Content of antimicrobial composition in polymer composition (%) | Micro-organism | No. of viable cells per sample | | |
|---|---|---|---|---|---|
| | | | 0 | 5 | 12 (hr) |
| PVDC-1 | 1.5 | Escherichia coli | $8.7 \times 10^6$ | 0 | 0 |
| PVDC-2 | 3 | Escherichia coli | $8.9 \times 10^6$ | 0 | 0 |
| PVDC-BL | — | Escherichia coli | $9.2 \times 10^6$ | $8.8 \times 10^6$ | $8.3 \times 10^6$ |
| PVDC-2 | 3 | Aspergillus niger | $5.8 \times 10^6$ | $7.6 \times 10$ | 0 |
| PVDC-BL | — | Aspergillus niger | $6.1 \times 10^6$ | $5.7 \times 10^6$ | $5.4 \times 10^6$ |

The PVDC polymer compositions containing 1.5% and 3%, respectively, of the antimicrobial composition (PVDC-1 and PVDC-2) had strong antimicrobial activity against Escherichia coli and all cells were found to be dead after the passage of 5 hours. As Table 8 shows, PVDC-BL (blank test sample) did not exhibit any antimicrobial activity at all. In the test on fungal Aspergillus niger, PVDC-2 reduced the cell count to 7.6×10 per sample at 5 hours, which was equivalent to a death rate of at least 99.99%. On the other hand, PVDC-BL (blank test sample) had no antimicrobial activity at all. The above test results clearly show that the antimicrobial polymer compositions of the present invention have satisfactory antimicrobial and/or microbicidal activity.

EXAMPLE 5

This example relates to the preparation of a shaped polyvinyl chloride (PVC) containing an antimicrobial composition having silver as a microbicidal metal, as well as the evaluation of its antimicrobial activity.

The dried product of the antimicrobial composition containing silver as a microbicidal metal which was prepared in Example 1 (Ag=0.14 mmol per 100 m² of the surface area in anhydrous state; specific surface area, 324 m²/g as measured by $N_2$ adsorption in the BET method) was ground into fine particles and heated at 200°–210° C. under vacuum to a water content of 1.5% and below. The dried fine particles were mixed with PVC and the blend was shaped into PVC sheets by the following procedure. Fifty parts of a plasticizer (DOP) was added to 100 parts of PVC ("Nippolit SL" of general-purpose grade of Chisso Corporation; degree of polymerization, 1,000); after adding a stabilizer and a gelation accelerator in small amounts, the previously prepared fine particulate antimicrobial composition was added in such an amount that it would assume 2 or 3% of the resulting mixture. The mixtures were then heated at 140°–150° C. and homogenized by kneading on mixing rolls. The homogenized mixtures were shaped into sheets of a thickness of ca. 1.5 mm.

The shaped PVC was cut into small test pieces (ca. 50×50×1.5 mm) that were respectively designated PVC-1 and PVC-2. These samples were subjected to an antimicrobial activity test by the spray method. As a comparison, a PVC sheet containing no antimicrobial composition was prepared for use in a blank test in accordance with the method of preparing the above-described antimicrobial PVC sheets. This PVC sheet was cut into small test pieces, designated PVC-BL (ca. 50×50×1.5 mm). It was also subjected to an antimicrobial activity test by the spray method. The results are shown in Table 9 below.

TABLE 9

Antimicrobial Activity Test by the Spray Method (Example 5)

| Test sample | Content of antimicrobial composition in polymer composition (%) | Microorganism | No. of viable cells per sample | | |
|---|---|---|---|---|---|
| | | | 0 | 6 | 24 (hr) |
| PVC-1 | 2 | Staphylococcus aureus | $3.9 \times 10^6$ | 0 | 0 |
| PVC-2 | 3 | Staphylococcus aureus | $4.1 \times 10^6$ | 0 | 0 |
| PVC-BL | — | Staphylococcus aureus | $3.6 \times 10^6$ | $1.8 \times 10^6$ | $1.1 \times 10^6$ |

PVC-1 and PVC-2 which contained the antimicrobial composition in respective amounts of 2% and 3% were found to have killed all cells (cell count=0) at 6 hours. PVC-BL, the sample for the blank test, was not at all effective against the test microorganisms. The above results clearly show that the PVC polymer compositions containing the antimicrobial composition of the present invention exhibit remarkable microbicidal activity.

EXAMPLE 6

This example relates to the preparation of a PP (polypropylene) film containing an antimicrobial composition having both silver and zinc as microbicidal metals.

The dried product of the antimicrobial composition containing silver and zinc as microbicidal metals which was prepared in Example 2 (0.11 mmol Ag and 0.04 mmol Zn per 100 m$^2$ of the surface are an anhydrous state; specific surface area, 319 m$^2$/g as measured by N$_2$ adsorption in the BET method) was ground into fine particles and heated at ca. 200° C. under vacuum to a water content of 1.5% and below. The dried fine particles of the antimicrobial composition were mixed with PP (A4141 of Chisso Corporation) in such an amount that the former would assume 1.5% or 2.5% of the resulting mixture. The mixtures were then shaped into films 30 μm thick by inflation molding with the cylinder and die outlet being held at temperatures of 210°-220° C. and ca. 220° C., respectively, and with the screw rotating at 25 rpm. The resulting PP films were cut into small test pieces (PP-1 and PP-2 each measuring ca. 50 mm×50 mm×30 μm), which were subjected to an antimicrobial activity test. As a comparison, a PP film (30 μm thick) containing no antimicrobial composition was prepared as already described for use in a blank test. This film was cut into small test pieces (ca. 50 mm×50 mm×30 μm), designated PP-BL, and subjected to an antimicrobial test. The results are shown in Table 10 below.

TABLE 10

Antimicrobial Activity Test by the Spray Method (Example 6)

| Test sample | Content of antimicrobial composition in polymer composition (%) | Microorganism | No. of viable cells per sample | | |
|---|---|---|---|---|---|
| | | | 0 | 12 | 24 (hr) |
| PP-1 | 1.5 | Staphylococcus aureus | $7.3 \times 10^6$ | 0 | 0 |
| PP-2 | 2.5 | Staphylococcus aureus | $7.6 \times 10^6$ | 0 | 0 |
| PP-BL | — | Staphylococcus aureus | $7.9 \times 10^6$ | $5.1 \times 10^6$ | $3.9 \times 10^6$ |

TABLE 10-continued

Antimicrobial Activity Test by the Spray Method (Example 6)

| Test sample | Content of antimicrobial composition in polymer composition (%) | Microorganism | No. of viable cells per sample | | |
|---|---|---|---|---|---|
| | | | 0 | 12 | 24 (hr) |
| | | coccus aureus | $10^6$ | $10^6$ | $10^6$ |

When PP-1 and PP-2 films containing the antimicrobial composition of Example 2 respective amounts of 1.5% and 2% were used, the cell count of Staphylococcus aureus was zero at 12 hours, indicating the strong bactericidal activity of these samples. On the other hand, PP-BL film as the blank test sample was not at all effective against Staphylococcus aureus. These results clearly show that the PP polymer composition in film form which contained the antimicrobial composition of the present invention exhibit remarkable microbicidal activity.

EXAMPLE 7

This example relates to the preparation of HDPE (high-density polyethylene) monofilaments containing an antimicrobial composition having both silver and zinc as microbicidal metals.

The HDPE used in Example 7 was "Showrex F 5012M" having melt index (M.I.) of 1.2. The dried product of the antimicrobial composition containing silver and zinc as microbicidal metals which was prepared in Example 2 (0.11 mmol Ag and 0.04 mmol Zn per 100 m$^2$ of the surface area in anhydrous state; specific surface area, 319 m$^2$/g by N$_2$ adsorption in the BET method) was ground with a jet mill to fine particles having an average size of 15 μm. These particles were heated at ca. 210° C. under vacuum to a water content of 1.5% and below. The dried fine particles of the antimicrobial composition were mixed with HDPE in such an amount that the former would assume 1.5% or 3% of the resulting mixture on a dry basis. The mixtures were then shaped into HDPE monofilaments of an antimicrobial polymer composition by extrusion molding under the following conditions: temperature, 225°±5° C.; pressure, ca. 100 kg/cm$^2$.G; residence time, 10–12 minutes; throughput, 1.5 kg/hr; screw rotating speed, 20 rpm; length (L) to diameter (D) ratio of screw, L/D≈25. The monofilaments were drawn at a ratio of ca. 10 to a fineness of ca. 400 denier. The resulting monofilaments were designated HDPE-1 and HDPE-2.

These monofilaments (ca. 400 d) had satisfactory strength. A portion (1 g) of them was subjected to an antimicrobial activity test by the shake flask method already described herein. The results are shown in Table 11 below.

TABLE 11

Antimicrobial Activity Test by Shake Flask Method (Example 7)

| Test sample | Content of antimicrobial composition in polymer composition (%) | Microorganism | No of viable cells per sample | | |
|---|---|---|---|---|---|
| | | | 0 | 6 | 24 (hr) |
| HDPE-1 | 1.5 | Escherichia coli | $5.3 \times 10^4$ | 0 | 0 |
| HDPE-2 | 3 | Escherichia coli | $7.8 \times 10^4$ | 0 | 0 |

TABLE 11-continued

Antimicrobial Activity Test by Shake Flask Method (Example 7)

| Test sample | Content of antimicrobial composition in polymer composition (%) | Micro-organism | 0 | 6 | 24 (hr) |
|---|---|---|---|---|---|
| HDPE-BL | — | Escherichia coli | $7.3 \times 10^4$ | $7.0 \times 10^4$ | $6.8 \times 10^4$ |
| HDPE-2 | 3 | Aspergillus niger | $3.9 \times 10^4$ | $5.4 \times 10$ | 0 |
| HDPE-BL | — | Aspergillus niger | $3.4 \times 10^4$ | $3.1 \times 10^4$ | $2.6 \times 10^4$ |

When HDPE-1 and HDPE-2 monofilaments containing the antimicrobial composition of Example 2 in respective amount of 1.5% and 3% were used, the cell count of bacterial Escherichia coli was zero at 6 hours, indicating the strong bactericidal activity of these samples. On the other hand, HDPE-BL as the blank test sample containing no antimicrobial composition was not at all effective against Escherichia coli. When HDPE-2 monofilaments containing said antimicrobial composition in an amount of 3% was used, the cell count of fungal Aspergillus niger was $5.4 \times 10$ cells per ml at 6 hours, which was equivalent to a death rate of 99.9%. When 24 hours passed, all cells were found dead. On the other hand, HDPE-BL monofilaments as the blank test sample were not at all effective against Aspergillus niger. These results clearly show that the HDPE monofilaments containing the antimicrobial composition of the present invention exhibit strong microbicidal action.

EXAMPLE 8

This example relates to the preparation of a shaped part of PS (polystyrene) containing an antimicrobial composition having silver supported as a microbicidal metal, as well as the evaluation of its antimicrobial activity.

The dried product of the antimicrobial composition containing silver as a microbicidal metal which was prepared in Example 1 (Ag=0.14 mml per 100 m² of the surface area in anhydrous state; specific surface area, 324 m²/g as measured by $N_2$ adsorption in the BET method) was ground into fine particles and heated at 200°–210° C. under vacuum to a water content of 1.5% and below. The dried fine particles were mixed with PS and a shaped PS part having a thickness of ca. 1.5 mm was prepared by the following procedure. The fine particles of the antimicrobial composition were added to PS ("Denka Styrol GD-1-301") in such an amount that the former would assume 0.70% of the resulting mixture. The mixture was then heated to 165°–170° C. and melted at the same temperature in a kneader. The melt was subsequently extrusion molded to a part having a thickness of ca. 1.5 mm. The shaped part was cut into small test pieces, PS-1, measuring ca. 50 mm × 50 mm × 1.5 mm. As a comparison, small test pieces, PS-BL (ca. 50 mm × 50 mm × 1.5 mm), containing no antimicrobial composition were prepared by the same procedure of molding for use in a blank test. The test results are shown in Table 12 below.

TABLE 12

Antimicrobial Activity Test by the Spray Method (Example 8)

| Test sample | Type and Amount of microbicidal agent (%) | Microorganism | No. of viable cells per sample 0 | 6 | 12 | 48 (hr) |
|---|---|---|---|---|---|---|
| PS-1 | microbicidal solid particles, 0.70% | Escherichia coli | $5.5 \times 10^5$ | $1.2 \times 10^2$ | 0 | 0 |
| PS-BL | — | Escherichia coli | $5.3 \times 10^5$ | $5.0 \times 10^5$ | $4.7 \times 10^5$ | $4.1 \times 10^5$ |
| PS-2* | antimicrobial zeolite, 1.0% | Escherichia coli | $5.1 \times 10^5$ | $7.6 \times 10^4$ | $5.8 \times 10^2$ | 0 |

*Comparative Example

COMPARATIVE EXAMPLE

In this comparative example, a shaped PS part (1.5 mm thick) containing 1.0% NaAgZ (the formula for antimicrobial zeolite, in which Ag=3.95% on a dry basis, and Z represents the matrix of zeolite A was prepared using the fine powder of NaAgZ and PS (the same as used in Example 8) by a method that was identical to that used in Example 8. The shaped part was cut into small test pieces, PS-2 (ca. 50 mm × 50 mm × 1.5 mm), for use as a comparison which was subjected to an antimicrobial activity test under the same conditions as adopted in Example 8. The results are also shown in table 12.

As Table 12 shows, the sample PS-1 (Example 8) containing 0.70% of the antimicrobial composition of the present invention exhibited strong bactericidal activity against Escherichia coli and its cell count dropped to $1.2 \times 10^2$ per sample at 6 hours, which was equivalent to a death rate of 99.98%. At 12 hours, all cells of Escherichia coli were found dead. In contrast, the PS-BL sample (for use in blank test) containing no antimicrobial composition was not at all effective against Escherichia coli. The PS-2 sample (Comparative Sample) containing 1.0% antimicrobial zeolite exhibited microbicidal action against Escherichia coli and its cell count was $7.6 \times 10^4$ and $5.8 \times 10^2$ per sample at 6 hours and 12 hours, respectively. The former value was equivalent to a death rate of 85.1% and the latter to 99.9%. Comparing the cell count profiles of PS-1 and PS-2, one can readily see that the former sample exhibited stronger bactericidal activity than the latter.

PS-1 (Example 8) containing 0.7% of the antimicrobial composition of the present invention had a Ag content of 0.034%, whereas PS-2 (Comparative Sample) containing 1.0% of antimicrobial zeolite had a Ag content of 0.039%. PS-2 contained silver in a slightly larger amount than PS-1 and yet, from the viewpoint of antimicrobial efficacy, PS-1 was superior to PS-2.

This difference in antimicrobial effect would have resulted from the essential structural difference between the antimicrobial composition of the present invention and the antimicrobial zeolite that were added to the polymer. For example, the differences in the pores in the matrix and the distribution of microbicidal metals result in the differences in antimicrobial effect between the two samples (see the previous discussion of the features and advantages of the polymer composition containing the antimicrobial composition of the present invention). As already mentioned, the PS sample containing the antimicrobial composition used in Example 8 had a silver content of 0.034%. Silver in the antimicrobial composition used in the antimicrobial activity test was not distributed uniformly in the silica gel matrix but distributed on the surfaces of great many pores in the silica gel (which were much larger than the pores in antimicrobial zeolite) by ionic bonding, with the Ag content amounting to 0.14 mmol/100 m$^2$. On the other hand, NaAgZ (pore size, 4 Å) used as the comparative example contained 0.039% Ag in PS. In sharp contrast from the antimicrobial composition used in Example 8, the comparative NaAgZ had Ag distributed uniformly in the zeolite matrix. The silver content in the polymer was 0.034% in Example 8 and it was distributed on the active surfaces of pores in silica gel. On the other hand, the silver content of the polymer in the comparative sample was 0.039% which differed from the silver content of the sample of Example 8 only slightly. However, as already mentioned, the silver in the antimicrobial composition used in Example 8 was distributed only on the active surfaces of pores in silica gel, so the amount effective silver available for microbicidal purposes was greater than that of silver in NaAgZ and the effective availability of microbicidal Ag in the composition of Example 8 was much higher than that of Ag in NaAgZ used as the comparison. Further, for the reasons already stated hereinbefore, microbicidal metal ions formed as a result of dissociation diffuse more rapidly in pores in the amtimicrobial composition of the present invention than in pores in the antimicrobial zeolite. Hence, the composition of the present invention should have a higher microbicidal efficiency than the antimicrobial zeolite and this is supported by the data shown in table 12.

EXAMPLE 9

This example relates to the preparation of an antimicrobial composition for use in aqueous systems that contains silver as a microbicidal metal.

Three liters of desalted water was added to ca. 1.5 kg of crushed silica gel (product of Nishio Kogyo K.K.; specific surface area, 450 m$^2$/g; pore size, 75 Å; pore volume, 0.8 cm 3/g; particle size, 30–60 mesh). The mixture was stirred at ca. 600 rpm to form a homogeneous slurry. To the slurry, a ca. 0.4N NaOH solution was added slowly until the pH of the slurry was finally adjusted to 9.5–10. Then, a solution having ca. 65 g of NaAlO$_2$ dissolved in 3 l of water was added to the slurry and the mixture was stirred at 25°±1° C. for ca. 11 hours at 600 rpm. After stirring, the mixture was filtered and the solid phase was washed with water to remove excess alkali and unreacted NaAlO$_2$. During the washing, the pH of the filtrate was finally held at about 9. To the solid phase, a ca. 0.69M solution of silver nitrate was added and the resulting mixture was stirred continuously at 25°±1° C. over a period of ca. 8 hours at 600 rpm. After the reaction, the mixture was filtered and the solid phase was washed with water to remove excess silver ions. The washed product was dried at 100°–110° C. to obtain a dried antimicrobial composition for use in aqueous systems which contained silver as a microbicidal metal according to the present invention.

This composition had a specific surface area and a pore volume of 328 m$^2$/g (as measured by N$_2$ adsorption in the BET method) and 0.73 cm$^3$/g, respectively. The amount of silver as determined was 5.13% (on a dry basis). The composition contained 0.145 mmol of silver per 100 m$^2$ of the surface area on a dry basis (see Table 13 below).

TABLE 13

| Antimicrobial Composition for Use in Aqueous Systems (Example 9) | | |
|---|---|---|
| Pore volume (cm$^3$/g) | Specific surface area (m$^2$/g) | Silver (mmol/100 m$^2$) |
| 0.73 | 328 | 0.145 |

In order to test the antimicrobial and/or microbicidal activity of the antimicrobial composition for use in aqueous systems which was prepared in Example 9, sewage was diluted with water to prepare two models of wastewater as follows:

Model 1: COD=58 mg/l; *E. coli* count=3.1×10$^5$/ml
Model 2: COD=91 mg/l; *E. coli* count=4.6×10$^5$/ml
(COD: Chemical oxygen demand)

Four grams of the dried product of the antimicrobial composition prepared in Example 9 was added to 500 ml of wastewater Model 1. The same dried product was added in an amount of 6 g to 500 ml of Model 2. Both models were then stirred at 20°–25° C. for 10 hours at 500 rpm. Thereafter, the death rate of *Escherichia coli* in the wastewater was measured in the usual manner.

The death rate of *Escherichia coli* was 100% in both wastewater Models 1 and 2, demonstrating the high bactericidal activity of the antimicrobial composition for use in aqueous systems which was prepared in Example 9.

In order to check the water resistance of the antimicrobial composition of the present invention for use in aqueous systems and its ability to maintain the microbicidal activity, the following test was conducted using the antimicrobial composition prepared in Example 9.

About twenty grams of the composition (dried product; particle size, 30–60 mesh) was charged into a small glass ion-exchange column having an inside diameter of 22 mm. After backwashing with water, the composition was uniformly packed to form a bed. Tap water (Ca$^{2+}$=17 ppm; Mg$^{2+}$=6.9 ppm; Cl=33 ppm; pH=6.7) was passed through the column at a flow rate of 30±1.5 ml/min. When the amount of effluent emerging from the bottom of the column reached predetermined levels (see Table 14 below), a portion of the effluent was sampled and the concentration of silver in it was measured by atomic-absorption spectroscopy. The results are shown in table 14.

TABLE 14

| Water Passage Test | |
|---|---|
| Effluent (l) | Silver in effluent (ppb) |
| 10 | 5 |
| 30 | 6 |
| 70 | 5 |
| 100 | 4 |
| 200 | 7 |
| 300 | 6 |
| 500 | 6 |

As Table 14 shows, satisfactory results were obtained since the content of silver in all samples of the effluent was very low within the range of 4–7 ppb. Throughout the passage of water, the composition experienced no breakage, deformation, wear and other deterioration, indicating the good water resistance of the composition.

After passing 500 l of water through the column, the spent antimicrobial composition was taken out of the column and the retention of its antimicrobial and/or microbicidal activity was checked by the following procedure. a suspension (1 ml) containing no more than 10⁴ spores per ml of *Aspergillus niger* was injected and mixed with 9 ml of a suspension of the spent composition (300 mg/ml) and the mixture was held at 30° C. for 24 hours. A portion (0.1 ml) of the mixture was dispersed in a Sabouraud's agar medium and left to stand at 30° C. for 48 hours. Thereafter, the number of viable cells was counted to calculate the death rate of *Aspergillus niger*, which was 100%. The test results clearly show that the antimicrobial composition of the present invention for use in aqueous systems have strong antimicrobial and/or microbicidal activity and exhibit the intended effect in water for a long time.

What is claimed is:

1. An antimicrobial composition composed of a coat of aluminosilicate on the surface of silica gel, wherein said composition has a pore volume of at least 0.3 cm³/g and a specific surface area of at least 100 m²/g, wherein said aluminosilicate coat is composed of either partial or complete substituted ion-exchangeable metal (M) in the aluminosilicate solid coating layer represented by the formula $$xM_{2/n}O \cdot Al_2O_3 \cdot ySiO_2 \cdot ZH_2O,$$

wherein x and y represent the numbers of molecules of the metal oxide and silicon dioxide, respectively, M is an ion-exchangeable metal, n is the atomic valence of M, and z is the number of molecules of water, and wherein said partial or completely substituted ion-exchangeable metal is selected from the group consisting of silver, copper, zinc, mercury, tin, lead, bismuth, cadmium, chromium and mixtures thereof.

2. An antimicrobial composition according to claim 1, wherein the metal ions having microbicidal action are present in a total amount of at least 0.003 mmol per 100 m² of the surface coating of said composition.

* * * * *